United States Patent [19]

Supernaw

[11] Patent Number: 4,977,319
[45] Date of Patent: Dec. 11, 1990

[54] METHOD FOR DETERMINING OIL CONTENT OF AN UNDERGROUND FORMATION

[75] Inventor: Irwin R. Supernaw, Houston, Tex.

[73] Assignee: Texaco Inc., White Plains, N.Y.

[21] Appl. No.: 307,118

[22] Filed: Feb. 3, 1989

Related U.S. Application Data

[63] Continuation-in-part of Ser. No. 201,729, Jun. 3, 1988, abandoned.

[51] Int. Cl.⁵ ............................................. G01N 21/64
[52] U.S. Cl. .................................... 250/255; 250/301; 250/461.1
[58] Field of Search ...................... 250/301, 255, 461.1; 356/70

[56] References Cited

U.S. PATENT DOCUMENTS

| Re. 22,081 | 4/1942 | Campbell | 250/255 |
| 2,311,151 | 2/1943 | Campbell | 250/71 |
| 2,337,465 | 12/1943 | Heigl | 250/255 |
| 2,403,631 | 7/1946 | Brown | 250/255 |
| 2,459,512 | 1/1949 | Fash et al. | 250/71 |
| 2,591,737 | 4/1952 | Souther | 250/71 |
| 2,951,940 | 9/1960 | Graham et al. | 250/71 |
| 3,205,353 | 9/1965 | Bray | 250/43.5 |
| 4,248,599 | 2/1981 | Mommessin | 73/32 R |
| 4,609,821 | 9/1986 | Summers | 250/255 |
| 4,696,903 | 9/1987 | Owen | 436/28 |

OTHER PUBLICATIONS

Chisholm, B. R., Eldering, H. G. et al., Total Luminescence Contour Spectra of Six Topped Oils, BETC/RI--76/16, (Nov. 1966), prepared for ERDA in Bartlesville Energy Center.
Brownrigg, J. T. et al., Low Temperature Total Luminescence Contour Spectra of Six Topped Oils and Their Vacuum Distillate and Residuum Fractions, BETC RI-78/13, prepared for DOE for the Bartlesville Energy Technology Center. Hemphill, W. R. et al., Laboratory Analysis and Airborne.
Detection of Materials Stimulated to Luminesce by the Sun, Journal of Luminescence, vol. 31 and 32, pp. 724–726, North-Holland, Amsterdam, (1984).
Skoog, Douglas, Principles of Instrumental Analysis, Saunders College Publishing, Philadelphia, (3rd Ed. 1985), pp. 225–240.

Primary Examiner—Carolyn E. Fields
Attorney, Agent, or Firm—Jack H. Park; Kenneth R. Priem; Harold J. Delhommer

[57] ABSTRACT

The invention is a method of evaluating a sample of an underground formation to determine the hydrocarbon content of any hydrocarbons present in the formation. It involves the steps of solvating a known volume of a sample in a known volume of a solvent which will solvate hydrocarbons, quantitatively measuring with a fluorometer the emission fluorescence below about 400 nanometers of the solvated sample at an excitation wavelength at which most petroleum compounds fluorescence, and determining the hydrocarbon content of any hydrocarbon present in the sample by comparing the emission fluorescence of said solvated sample to previous correlations. The previous correlations are drawn between known hydrocarbon contents of samples and the emission fluorescence of the known samples in said solvent.

8 Claims, 1 Drawing Sheet

METHOD FOR DETERMINING OIL CONTENT OF AN UNDERGROUND FORMATION

This is a continuation-in-part of U.S. patent application Ser. No. 07/201,729, filed June 3, 1988, abandoned.

BACKGROUND OF THE INVENTION

This invention is related to techniques for determining the presence of hydrocarbons in an underground formation. More particularly, the invention offers a method for determining the oil saturation of a hydrocarbon formation from samples such as drill cuttings.

Because of the cost and time involved in placing wells on test to determine if certain intervals contain hydrocarbons or brine, it is desirable to have a logging method which accurately tells the well operator whether any hydrocarbons are present, and the saturation of such hydrocarbons. This is particularly true when a wildcat well is being drilled in an area with relatively unknown geology. Generally, current techniques are often ineffective in evaluating the oil content of an underground formation prior to placing a well on test.

In some situations, electric logs do not effectively differentiate between hydrocarbons and water. Although logging techniques indicate areas which are likely to contain brine instead of hydrocarbons or less saline water, their lack of discrimination between hydrocarbons and less saline water requires educated guesses. Because an operator does not want to overlook the presence of hydrocarbons, a frequent mistake is to place a zone on test and produce water. Such tests cost money and time. But an even more costly mistake is the failure to test a zone because the zone is thought to contain water, or to test an interval bigger than the true oil interval, producing a large flux of water and a small flux of oil. It is unknown how many times such mistakes are made.

Fluorescence has been used as a logging technique for detecting oil in drill cuttings for decades. However, the method used to determine the fluorescence of samples at a rig site is a crude method which has not improved appreciably and is severely limited in its usefulness and applicability. At present, fluorescence is determined when an operator shines a broad spectrum ultraviolet light source on cuttings in the hope of seeing substantial fluorescence to indicate the presence of oil. See U.S. Pat. Nos. 2,311,151; 2,337,465; 2,459,512; 2,951,940 and U.S. Pat. No. Re. 22,081.

There are several inherent problems in current fluorescence logging which make it nonquantitative at best and misleading at worst. First, the excitation source is not concentrated in the spectral region where the oil is most likely to absorb radiation and re-emit that radiation as fluorescence. Second, the oil is quite likely to emit fluorescence at wavelengths predominantly, if not totally, unseen by the human eye. Third, the fluorescence observed by the operator is influenced by the presence of fluorescent minerals such as fluorite. Fourth, the presence or amount of oil on the surface of the cuttings samples may not be representative of the oil in the pore structure of the formation. The mud logger sees only the surface of the samples with this technique. Fifth, operators' description of such fluorescence phenomena is highly subjective. Such commonly used words as strong, weak, bright, dull, yellow, and gold prohibit any quantitative analysis of the data.

In an attempt to overcome the subjectivity of fluorescent examination of formation samples, U.S. Pat. No. Re. 22,081 disclosed a method wherein the fluorescence of samples of known oil concentrations are visually compared by a technician to the unknown sample under the same exciting UV radiation. However, this method still retains considerable subjectivity. Most importantly, the process fails to measure emitted "invisible" fluorescence below 400 nm, the spectral region where trace amounts of oil are most likely to fluoresce with measurable intensity.

U.S. Pat. No. 2,311,151, having the same inventor as the above U.S. Pat. No. Re. 22,081, discloses two improvements wherein the emitted radiation of the U.S. Pat. No. Re. 22,081 process is (1) measured by a photoelectric cell, and (2) adjusted with a formula to compensate for the variations in surface area of the samples measured. But the improved process of U.S. Pat. No. 2,311,151 as well as U.S. Pat. No. Re. 22,081 fails to measure fluorescence below the visible spectrum.

U.S. Pat. No. 4,696,903 discloses shining UV light on formation samples and visually noting the color of the fluorescence as well as taking video pictures of the fluorescence for later study. U.S. Pat. No. 4,248,599 discloses a process for determining the API gravity of oil by the use of a flame ionization detector. In this method, the volatile and pyrolyzable components of oil are vaporized. A measurement is made of the ratio of the amount of hydrocarbon vapor produced at temperatures within a selected high temperature range to the total amount of vapor produced. A ratio of fluorescence measured under two conditions is taken in conjunction with the use of the flame ionization detector.

U.S. Pat. No. 2,591,737 detects oil by subjecting drilling fluid to steam distillation and visually inspecting the product for crude oil fractions, optionally, under UV light. U.S. Pat. No. 3,205,353 uses IR and UV light to detect contamination of underground formation samples by drilling fluid.

Hemphill, W. R. et al., "Laboratory Analysis and Airborne Detection of Materials Stimulated to Luminesce By the Sun", Vol. 31 and 32, p. 724–6, North-Holland, Amsterdam (1984) discusses the use of an airborne electro-optical device used to detect the luminescence intensity of target materials at visual wavelengths above 450 nm. Suggested uses are to detect uranium, marine oil seeps, stressed vegetation, and pollution effluents.

The emission fluorescence of crude oil samples has been studied and recorded over various wavelengths, including ultraviolet wavelengths below 400 nm. Studies which have taken place at the Bartlesville Energy Technology Center have been basically "fingerprint" studies wherein the emission fluorescence of various types of crude oils has been recorded at different excitation wavelengths. This Department of Energy research was a spin-off from earlier efforts by the Bureau of Mines to try to identify crude oil by emission fluorescence for purposes of pollution control. Please see Chisholm, B. R., Eldering, H. G., Giering, L. P., and Hornig, A. W., Total Luminescence Contour Spectra of Six Topped Crude Oils, BETC/RI-76/16, a paper prepared for ERDA for the Bartlesville Eneregy Research Center in Bartlesville, Okla., November 1976; and Brownrigg, J. T. and Hornig, A. W., Low Temperature Total Luminescence Contour Spectra of Six Topped Crude Oils and their Vacuum Distillate and Residuum Fractions, BETC/RI-78/13, a paper prepared for DOE for the Bartlesville Energy Technology Center, Bartlesville, Okla., July 1978. Similar, non-published fingerprinting work of crude oils by total luminescence spectra has also been performed in unpublished work at Texas A. & M. University.

There is one recently developed process which employs fluorescent measurement to test for the presence of hydrocarbons within drill cuttings. But this process does not give an indication of viscosity or producibility. Further, U.S. Pat. No. 4,609,821 is applicable only to oil base mud drill cuttings. The cuttings are excited with a wide range of UV wavelengths and the emitted radiation is recorded over a wide range of wavelengths to produce an analytical chemical profile. This profile of intensity over multiple wavelengths of excitation and emission radiation is compared with previous profiles to determine the presence of hydrocarbons not associated with the oil base mud.

Molecular fluorescence is discussed in general in Skoog, Douglas, *Principles of Instrumental Analysis*, Sanders College Publishing, Philadelphia (3rd ed. 198), pp. 225-240. The reference indicates that the greatest fluorescence behavior occurs with compounds containing aromatic functional groups and offers a table which indicates the UV fluorescence wavelengths associated with numerous benzene derivatives in ethanol solution. Several analytical profiles of hydrocarbons are disclosed wherein fluorescence intensity is plotted over multiple excitation and emission wavelengths.

SUMMARY OF THE INVENTION

The invention is a method of evaluating a sample of an underground formation to determine the hydrocarbon content of any hydrocarbons present in the formation. It involves the steps of solvating a known volume of a sample in a known volume of a solvent which will solvate hydrocarbons, quantitatively measuring the emission fluorescence below about 400 nanometers of the solvated sample at an excitation wavelength at which most petroleum compounds fluoresce, and determining the hydrocarbon content of any hydrocarbon present in the sample by comparing the emission fluorescence of said solvated sample to previous correlations. The previous correlations are drawn between known hydrocarbon contents of samples and the emission fluorescence of the known samples in said solvent.

DETAILED DESCRIPTION

Figure 1:
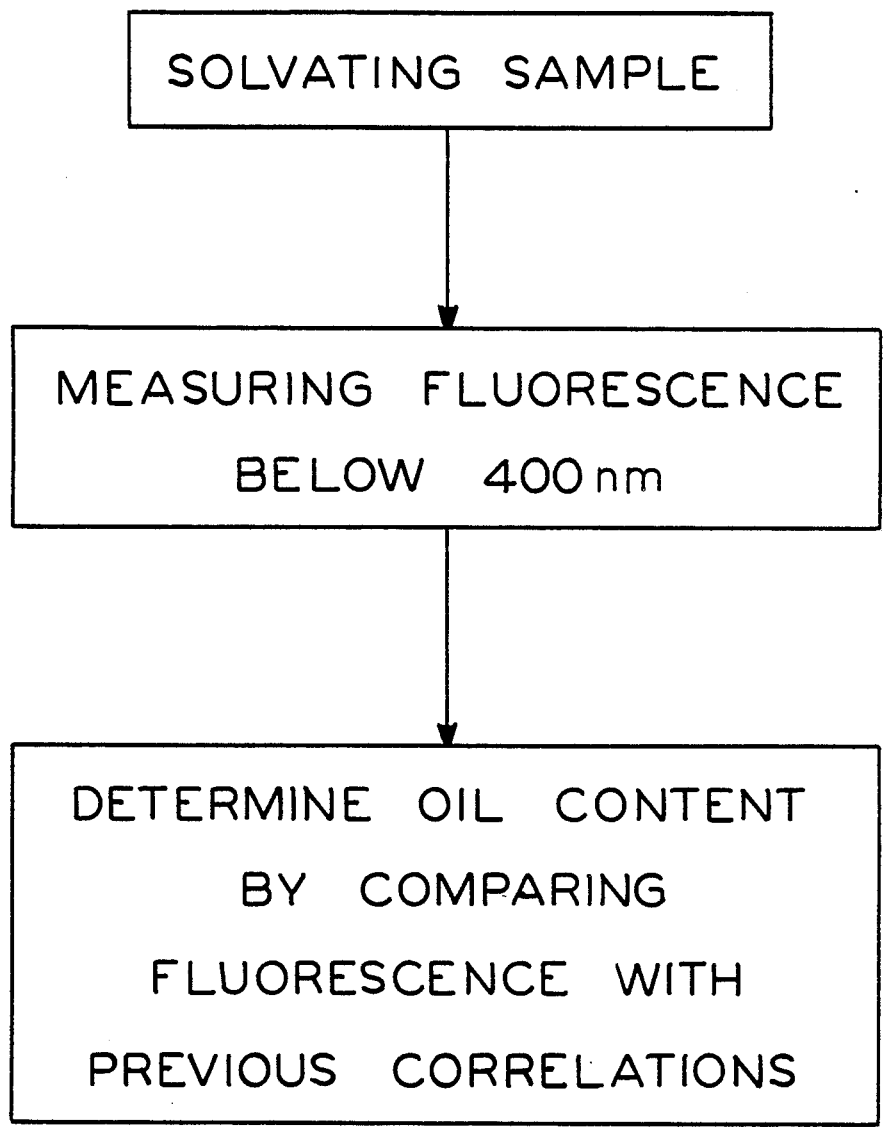
FIG. 1 is a flowchart of the invention method.

Fluorescence is a phenomena wherein certain compounds, containing molecular arrangements generally referred to as chromophores, emit fluorescent radiation when excited by incoming light of certain wavelengths. The chromophores contained in compounds such as the asphaltenic, aromatic and resin fractions of crude, fluoresce in the UV portion of the electromagnetic spectrum when bombarded with radiation of the proper excitation wavelength.

A technique known as total scanning fluorescence or 3-D fluorescence has been developed, wherein a sample is excited over a range of discrete wavelengths and the emitted radiation is recorded at various wavelengths. Total scanning fluorescence has indicated that the optimum excitation and emission wavelengths for most crude oils falls below 400 nanometers. This is a region where the human eye has no response. The optimum excitation wavelength for most crude oils is in the region of about 250 to about 310 nanometers. The predominant portion of emitted radiation falls in the nonvisible ultraviolet region of about 250 to about 400 nanometers.

By using a scale of fluorescence intensity and instrumentally measuring the fluorescence of a formation sample from a core or drill cuttings, we have discovered that we can derive a number proportional to the hydrocarbon content of the sample. Thus, by examining drill cuttings on site, it can be determined whether or not a underground interval or zone contains hydrocarbons and the approximate concentration of such hydrocarbons without putting a well on test.

Hydrocarbon content is determined by first solvating a known volume of sample of the formation in a known volume of a solvent which will solvate hydrocarbons. The emission fluorescence below about 400 nanometers is quantitatively measured by a fluorometer for the solvated sample at a fixed, relatively narrow, band of excitation wavelengths at which most petroleum compounds fluoresce. This value is proportional to the hydrocarbon content of the sample. By comparing the emission fluorescence of the solvated sample with previous correlations, the hydrocarbon content of the sample may be determined. The previous correlations can be drawn between known oil concentration of samples and the fluorescence of the known samples in said solvent.

Preferably, a single fluorescence intensity measurement is obtained for each sample rather than multiple intensity measurements at multiple excitation wavelengths. However, since different crude components and minerals fluoresce at different wavelengths, it may be desirable to obtain multiple intensity measurements of one sample at different wavelengths in order to decrease the influence of a particular component in the drill cuttings. For example, an additive in a drilling mud may fluoresce strongly around 250 nm and not fluoresce strongly at about 300 nm. To substantially eliminate the effect of the additive, it may be desirable to change the excitation or emission wavelength from around 250 nm to about 300-310 nm or about 320-330 nm. Such changes can be made by adjusting or changing the source lamp, the excitation filter or the emission filter of the fluorometer.

Since the fluorescence of a sample is proportional to the oil concentration within the sample, an accurate measurement of fluorescence plugged into the proper equation derived from previous correlations will yield the oil concentration of the sample. The oil concentration plus the known weight, volume and porosity of the sample, and the volume of the solvent can be used to calculate the oil saturation of the sample.

A wide variety of solvents capable of solvating hydrocarbons may be used in the invention. Preferred solvents are low molecular weight aliphatic hydrocarbons having more than four carbon atoms such as pentane, hexane, heptane and higher. Chlorinated hydrocarbons such as methylene chloride, chloroform, carbon tetrachloride, trichloroethane and others are also effective. But strong solvents may lessen the accuracy of the invention method due to their ability to dissolve other sample constituents than hydrocarbons. Aromatic solvents are generally not preferred because of their inherent fluorescence.

The following examples will further illustrate the novel method of determining oil content from formation samples by the present invention. These examples are given by way of illustration and not as limitations on the scope of the invention. Thus, it should be understood that the steps of the invention method may be varied to achieve similar results within the scope of the invention.

EXAMPLES

In the following examples, oil saturation was determined for two different samples. A Sequoia Turner Model 112 fluorometer was employed in the Examples. The Turner Model 112 fluorometer consists basically of an ultraviolet light source, an excitation radiation filter between the light source and the sample, a photomultiplier tube which reads the intensity of radiation emitted by the sample at right angles to the excitation radiation, and an emission filter placed between the sample and the photomultiplier tube. A reference light path between the light source and the photomultiplier is also provided so that the difference between emitted radiation and exciting radiation can be easily determined.

The light source employed for these examples was a far ultraviolet source U tube having Turner Model No. 110-851, GE No. G4T4/1 or equivalent. 95% of the radiation from this light source is at 254 nm, with some output at 297, 313, 405, 436 and 546 nm.

The excitation radiation filter employed was a Turner No. 7-54 filter which has a bell-shaped radiation transmission curve. This filter transmits about 80% of the radiation which strikes it from about 290 to about 360 nm, and 40% or more of incident radiation from about 250 nm to about 390 nm. Only 10% of incident radiation is transmitted at 236 nm and 400 nm. The end result of this combination of light source and excitation radiation filter is that 99% of the excitation radiation used in Examples 1-2 was at 254 nm.

The emission filter employed was a 320 nm narrow band filter. The transmission curve of this emission filter allows 25% transittance of incident radiation at 320 nm, dropping steeply to 20% transmittance at 313 nm and 327 nm. Transmittance is only 4% at 310 nn and 330 nm.

The invention method is by no means limited to the combination of filters and light source employed with the Turner Model 112 fluorometer. Other fluorometers, light sources including lasers, and filters may be employed with the invention method with equal success. What the invention requires is that the solvated samples be radiated at an excitation wavelength at which most petroleum compounds fluoresce, generally below about 400 nm, and preferably about 250 nm to about 310 nm. The emission fluorescence must be measured below about 400 nm, preferably within the region of about 250 nm to about 400 nm. Although these examples were run with an excitation radiation of 254 nm and emission radiation measured at 320 nm, it may be desirable to change the wavelengths employed to better eliminate the effect of fluorescence from other components present in the drill cuttings, such as minerals, pipe dope, or filtrate of oil base muds.

Steps 1-6 set forth below were followed for each sample.

Step 1

Develop a calibration curve (X axis-fluorescence reading, Y axis-oil concentration). One calibration curve equation we have developed from previous correlations made between known oil concentration and fluorometer reading for multiple samples is $C_{oil} = mF + C = 0.7952(F) - 1.5101$. This equation should be approximately correct for most types of oil measured with the type of fluorometer employed in establishing the correlation equation. It is possible that the correlation equation for a viscous oil with a high concentration of chromophores or high aromatic content may be different due to greater fluorescence. These oils can be recognized by a fluorescent technique which isolates the fluorescence due to asphaltenes and aromatics. Such a technique is disclosed in U.S. patent application Ser. No. 07/278,316, filed Dec. 1, 1988, incorporated herein by reference. With such viscous oils, a correction factor may be employed with the correlation equation.

Step 2

Measure the fluorescence F (Fluorescence Intensity Units) of a weighed drill cutting sample in solvent volume $V_{sol}$.

Step 3

Determine the oil concentration in ppm from the calibration curve ($C_{oil}$).

Step 4

Calculate the pore volume of the sample.

$$PV_s \text{ (cc)} = \frac{\text{Wt. of Sample } (W_r) \text{ Porosity } (\phi)}{\text{Density } (\rho r)}$$

Step 5

Calculate the volume ($V_{oil}$) of oil in cc.

$$V_{oil} = \frac{(C_{oil})(V_{sol})}{10^6}$$

Step 6

$$\text{Oil Saturation in \% of Pore Volume} = \frac{V_{oil}}{PV_s}(100)$$

EXAMPLE 1

$W_r$ = 0.5 g
$\rho r$ = 2.67 g/cc
$\phi$ = 0.32
$V_{sol}$ = 5 cc
$F$ = 12,900

$$PV_s = \frac{0.5 (0.32)}{2.67} = 0.06 \text{ cc}$$

$$C_{oil} = \frac{C_{oil}(V_{sol})}{10^6}$$

$$C_{oil} = -1.5101 + 0.7952 (12,900) = 10,256.57 \text{ ppm}$$

$$V_{oil} = \frac{10,256 (5)}{10^6} = 0.051 \text{ cc}$$

$$\text{Oil Saturation} = \frac{V_{oil}}{PV_s}(100) = \frac{0.051}{0.060}(100) = 85.58\%$$

EXAMPLE 2

$F = 6480$ $W_r = 0.5 \text{ g}$ $pr = 2.67 \text{ g/cc}$ $\phi = 0.32$ $V_{sol} = 5 \text{ cc}$ $PV_s = \dfrac{0.5\,(0.32)}{2.67} = 0.06 \text{ cc}$ $C_{oil} = -1.5101 + 0.7952\,(6480) = 5151.39 \text{ ppm}$ $V_{oil} = \dfrac{5151.39\,(5)}{10^6} = 0.026 \text{ cc}$ $\text{Oil Saturation} = \dfrac{0.026 \text{ cc}}{0.06 \text{ cc}}\,(100) = 42.93\%$ Many other variations and modifications may be made in the concepts described by those skilled in the art without departing from the concepts of the present invention. Accordingly, it should be clearly understood that the concepts disclosed in the description are illustrative only and are not intended as limitations on the scope of the invention.

What is claimed is:

1. A method of evaluating a sample of an underground formation to determine the hydrocarbon content of the formation, which comprises:
   solvating a known volume of an underground formation sample in a known volume of a solvent which will solvate hydrocarbons;
   quantitatively measuring with a fluorometer the emission fluorescence of the solvated sample below about 400 nanometers at an excitation wavelength at which most petroleum compounds fluoresce; and
   determining the hydrocarbon content of any hydrocarbon present in the sample by comparing the emission fluorescence of said solvated sample to previous correlations,
   said previous correlations drawn between known hydrocarbon contents of samples and the emission fluorescence of the known samples in said solvent.

2. The method of claim 1, wherein the solvent which will solvate hydrocarbons is hexane, heptane, or pentane.

3. The method of claim 1, wherein the samples are drill cuttings.

4. The method of claim 1, wherein the emission fluorescence is measured between about 250 and about 400 nanometers.

5. The method of claim 1, wherein the solvated sample is excited between about 250 and about 310 nanometers.

6. The method of claim 1, wherein oil concentration of a sample is determined.

7. The method of claim 6, further comprising determining oil saturation from the oil concentration of the sample and the known weight, volume and porosity of the sample, and the volume of solvent.

8. A method of evaluating drill cuttings from an underground formation to determine the hydrocarbon content of the portion of the formation from which the cuttings came, which comprises:
   solvating a known volume of drill cuttings in a known volume of hexane;
   quantitatively measuring with a fluorometer the emission fluorescence of the solvated cuttings between about 250 and about 400 nanometers at a relatively narrow excitation wavelength band between about 250 and about 310 nanometers;
   determining the hydrocarbon content of any hydrocarbon present in the cuttings by comparing the emission fluorescence of said cuttings to previous correlations,
   said previous correlations drawn between known hydrocarbon contents of samples and the emission fluorescence of the known samples in hexane at said excitation wavelength band.

* * * * *